United States Patent [19]

Saffer

[11] Patent Number: 4,890,311
[45] Date of Patent: Dec. 26, 1989

[54] BIOPSY MEANS FOR AN X-RAY EXAMINATION APPARATUS

[75] Inventor: Edmund Saffer, Eggolsheim, Fed. Rep. of Germany

[73] Assignee: Siemens Aktiengesellschaft, Berlin and Munich, Fed. Rep. of Germany

[21] Appl. No.: 208,246

[22] Filed: Jun. 17, 1988

[30] Foreign Application Priority Data

Jun. 30, 1987 [DE] Fed. Rep. of Germany ....... 3721589

[51] Int. Cl.$^4$ .......................... H05G 1/64; H05G 5/30
[52] U.S. Cl. ....................................... 378/99; 378/205; 378/163; 606/185
[58] Field of Search .................. 378/99, 204, 205, 37, 378/162–164; 358/111; 128/303 B, 329 R

[56] References Cited

U.S. PATENT DOCUMENTS

| 4,485,815 | 12/1984 | Amplatz et al. | |
| 4,722,336 | 2/1988 | Kim et al. | 378/162 |
| 4,727,565 | 2/1988 | Ericson | 378/205 |
| 4,750,487 | 6/1988 | Zanetti | 378/162 |

FOREIGN PATENT DOCUMENTS

| 0146511 | 6/1985 | European Pat. Off. | |
| 2521000 | 8/1983 | France | |
| 2584601 | 1/1987 | France | |

OTHER PUBLICATIONS

Siemens Brochure, "Der Moderne Mammographie-Arbeitsplatz: MAMMOMAT B".

Primary Examiner—Carolyn E. Fields
Assistant Examiner—Joseph A. Hynds
Attorney, Agent, or Firm—Hill, Van Santen, Steadman & Simpson

[57] ABSTRACT

Biopsy assembly for use in an x-ray examination apparatus having an x-radiator with a focus from which a ray pyramid emanates, and a radiation receiver arranged residing opposite the x-radiator for producing an x-ray picture of an examination subject situated between the two, the biopsy assembly determining a paracentesis point of a biopsy needle pertaining to a diagnostically relelvant region imaged on the x-ray picture and situated inside the examination subject and positioning the biopsy needle relative thereto. The biopsy assembly includes a guide element having a channel for the biopsy needle with a diameter essentially corresponding to that of the biopsy needle, and a positioning system for adjusting the guide element relative to the region of the examination subject such that the longitudinal axis of the channel of the guide element always proceeds through the focus of the x-radiator.

10 Claims, 4 Drawing Sheets

BIOPSY MEANS FOR AN X-RAY EXAMINATION APPARATUS

BACKGROUND OF THE INVENTION

1. Field of the Invention

The invention is directed to a biopsy assembly for an x-ray examination apparatus having an x-radiator with a focus from which a ray pyramid emanates, and a radiation receiver arranged lying opposite thereto for generating an x-ray picture of an examination subject situated between the two.

2. Description of the Prior Art

Devices are known for the identification of a paracentesis point for a biopsy needle pertaining to a diagnostically relevant region imaged on the x-ray picture and situated within the examination subject. Such devices have a guide element for aligning the biopsy needle to the paracentesis point having a channel for the biopsy needle whose diameter essentially corresponds to that of the biopsy needle, and means for positioning the guide element relative to the examination subject.

A biopsy assembly for mammography is known from the advertising brochure of Siemens AG, "Der moderne Mammographie-Arbeitsplatz: MAMMOMAT B", Order number, A19100-M1087-A789-01. The known biopsy assembly has two scales describing an angle and being imagable on the x-ray picture. The scales are attached to a plate for compression of the examination subject. The scales are applied to the edge of an opening provided in the plate, the examination subject being accessible through this opening. Means are also provided that allow a shadow cross whose legs proceed parallel to the scales to be projected onto the examination subject. The legs of the shadow cross have a length such that they intersect the scales. The shadow cross is adjustable such that the position of the intersection of its legs can assume and arbitrary position on the region of the examination subjection accessible through the opening of the plate.

When an x-ray picture of the examination subject is prepared, the scales are imaged together with the examination subject. When the x-ray picture exhibits a diagnostically relevant region within the examination subject that is to be punctured or to be marked for a test, the coordinates of the region are determined on the x-ray picture with reference to the scales. Subsequently, the shadow cross is set to corresponding coordinates for determining the paracentesis point for the biopsy needle. For puncturing or marking, an incision is then made with the biopsy needle at the intersection of the legs of the shadow cross and the biopsy needle is advanced into the required depth. The paracentesis point identified in this way lies on a straight line that proceeds through the diagnostically relevant subject and through the focus of the x-radiator. The examination subject is not to be moved in the time span between the production of the x-ray picture and the execution of the puncture.

The known biopsy means is constructed in a very simple way and allows the paracentesis point for the biopsy needle to be determined with great precision with reference to a single x-ray picture, however, when the diagnostically relevant region is situated far inside of the examination subject, a risk exists that the biopsy needle will be conducted past the region. When this is not noticed, there is a risk of misdiagnosis. At the very least, the puncturing must be repeated, this being extremely uncomfortable for the patient.

This disadvantage is avoided in a biopsy assembly as disclosed in European Application 0 146 511. This biopsy assembly has means for the determination of a paracentesis point for the biopsy needle pertaining to a diagnostically relevant region, by a calculating operation with reference to two x-ray pictures exposed at different angles on which a stationary mark is imaged in addition to the diagnostically relevant region. This paracentesis point lies on a straight line that proceeds through the diagnostically relevant region and proceeds perpendicularly to the surface of a planar support for the examination subject. The known biopsy assembly also has a guide device for the biopsy needle with a channel whose longitudinal axis proceeds at a right angle relative to the surface of the support for the examination subject. Means for positioning the guide device are also provided with which the guide device is adjustable in the direction of the three spatial axes. For executing a puncture, the guide device is positioned such that the longitudinal axis of its channel proceeds through the identified paracentesis point and thus through the diagnostically relevant region. Although this makes it impossible for the biopsy needle to be conducted past the diagnostically relevant object, two x-ray pictures are required for the determination of the paracentesis point for the biopsy needle, resulting in an undesirable high radiation load on the examination subject. Further, the known x-ray device is constructed in a complicated fashion.

SUMMARY OF THE INVENTION

It is an object of the present invention to fashion a biopsy assembly of the general type described above, wherein it is possible to determine the paracentesis point with reference to a single x-ray picture and such that it is impossible for the biopsy needle to be conducted past the diagnostically relevant region.

This object is achieved in accordance with the principles of the present invention in an assembly wherein the means for determining a paracentesis point pertaining to a diagnostically relevant region are constructed such that the paracentesis point lies on a straight line that proceeds through the diagnostically relevant region and through the focus of the x-radiator, and wherein having a channel therein for guiding a biopsy needle is provided a guide device/which is automatically positionable such that the longitudinal axis of the channel proceeds through the focus of the x-radiator for arbitrary positions of the guide device relative to the examination subject. One proceeds in the puncturing or marking of a diagnostically relevant region such that a paracentesis point for the biopsy needle is first defined with reference to a corresponding x-ray picture with the assitance of the means for determining the paracentesis point for the biopsy needle. Since the means for determining the paracentesis point are fashioned such that the determined paracentesis point lies on a straight line that proceeds through the diagnostically relevant subject and the focus of the x-radiator, this is possible with reference to a single x-ray picture. The guide device is then brought into a position with a means for positioning the guide device such that the channel of the guide device proceeds through the identified paracentesis point. Since the means for positioning the guide device act automatically such that the longitudinal axis of the channel for arbitrary positions of the guide device proceeds through the focus of the x-radiator, it is assured that the diagnostically relevant region also lies on the longitudinal axis of the channel. When the biopsy needle is then introduced into the channel of the guide device and is then punctured into the examination subject and subsequently driven forward into the required depth, it is impossible for the biopsy needle to be conducted past the diagnostically relevant region.

If the radiation receiver emits electrical signals corresponding to the x-ray picture, these electrical signals being supplied to a video monitor for portrayal of the x-ray picture, it is provided in an embodiment of the invention that the means for determining the paracentesis point include means for mixing a mark, for example a graticule, into the x-ray picture portrayed on the video monitor and means for mixing the mark in the x-ray picture, and that the means for positioning the guide device are fashioned such that the latter is automatically adjustable under motor drive to a position relative to the examination subject such that the longitudinal axis of the channel proceeds through the fictitious position of the mark on the radiation receiver. It is only necessary then to displace the mark on the picture screen of the video monitor to the diagnostically relevant region and to actuate the means for positioning the guide device in order to bring the guide device into the required position. The puncturing or marking of the diagnostically relevant subject can follow immediately.

If there is no means for portraying the x-ray picture on a video monitor and the x-radiation receiver includes means for taking exposures, the means for determining the paracentesis point may have two scales situated in the ray pyramid that describe an angle and can be portrayed on the x-ray picture. The means for positioning the guide device then has two marking adjustable in common therewith, each of these markings interacting with one of the scales, whereby every marking is arranged relative to the channel such that the longitudinal axis thereof proceeds in a plane that intersects the corresponding scale at that point to which the marking is aligned and proceeds parallel to the respectively other scale. To undertake a biopsy, one first produces an x-ray exposure of the examination subject, both scales being visible thereon. Subsequently, the coordinates of a diagnostically relevant region are identified with reference to the scales and the guide device is brought into a position with the assistance of the markings interacting with the scales such that the markings are directed onto the points of the scales corresponding to the coordinates of the diagnostically relevant region. Since the markings are respectively arranged relative to the channel such that the longitudinal axis thereof proceeds in a plane that intersects the corresponding scale at that point to which the marking is aligned, it is guaranteed that the longitudinal axis of the channel proceeds through the diagnostically relevant subject.

An exemplary embodiment of the invention wherein the scales are arranged in the edge region of the ray pyramid has the following features.

The means for positioning the guide device has two rulers arranged in different planes, each of these rulers being allocated to one of the scales, proceeding at the right angle thereto, and being guided displaceable therealong. The rulers have a length such that they extend through the entire ray pyramid in every position. The markings interacting with the scales are each attached to the corresponding ruler at a distance from the longitudinal axis thereof. The rulers are each pivotable around an axis proceeding parallel to their respective longitudinal axis, with the respective pivoting of the rulers upon displacement thereof along the corresponding scale ensuing by means of an entraining mechanism such that the focus of the x-radiator, the marking and the axis of the respective ruler always lie in a common plane in which the longitudinal axis of the channel of the guide device also proceeds. Each of the rulers has a seating surface for the guide element that proceeds parallel to the corresponding, common plane and essentially extends over the entire length of the corresponding ruler. The guide device is formed by a guide element having a cube shape that can be introduced into the angle formed by the seating surfaces. Each of the rulers can be moved into a standby position outside of the ray pyramid.

The entraining mechanisms for pivoting the rulers can each be a stationary connecting link with which the corresponding ruler is in engagement with a projection attached thereto at a distance from the respective axis.

To prevent displacements of the guide device occurring during the execution of a puncturing or marking of a diagnostically relevant subject, the rulers may be locked to prevent displacements along the scales.

To be able to position the guide device with optimum precision, it is preferable that the marking of each ruler is arranged relative to the corresponding scale so that parallax errors are avoided.

To be able to employ biopsy needles having different diameters, it is expedient that the guide device in an embodiment of the invention is interchangeable. This is possible in a simple way by magnetically mounting the guide device.

It is also preferable in view of the hygiene to form the guide device by a guide element composed of two parts whose mating surfaces contain the channel, since simple cleaning of the guide element and of the channel is then guaranteed. Further, this structure offers the advantage that the biopsy needle can remain in the examination subject separated fro the biopsy assembly. This is advantageous especially when the examination subject is to be repositioned for producing a monitoring exposure or when the biopsy needle is to remain in the examination subject as a marking for a surgical operation following immediately thereafter.

DESCRIPTION OF THE PREFERRED EMBODIMENTS

Figure 1:
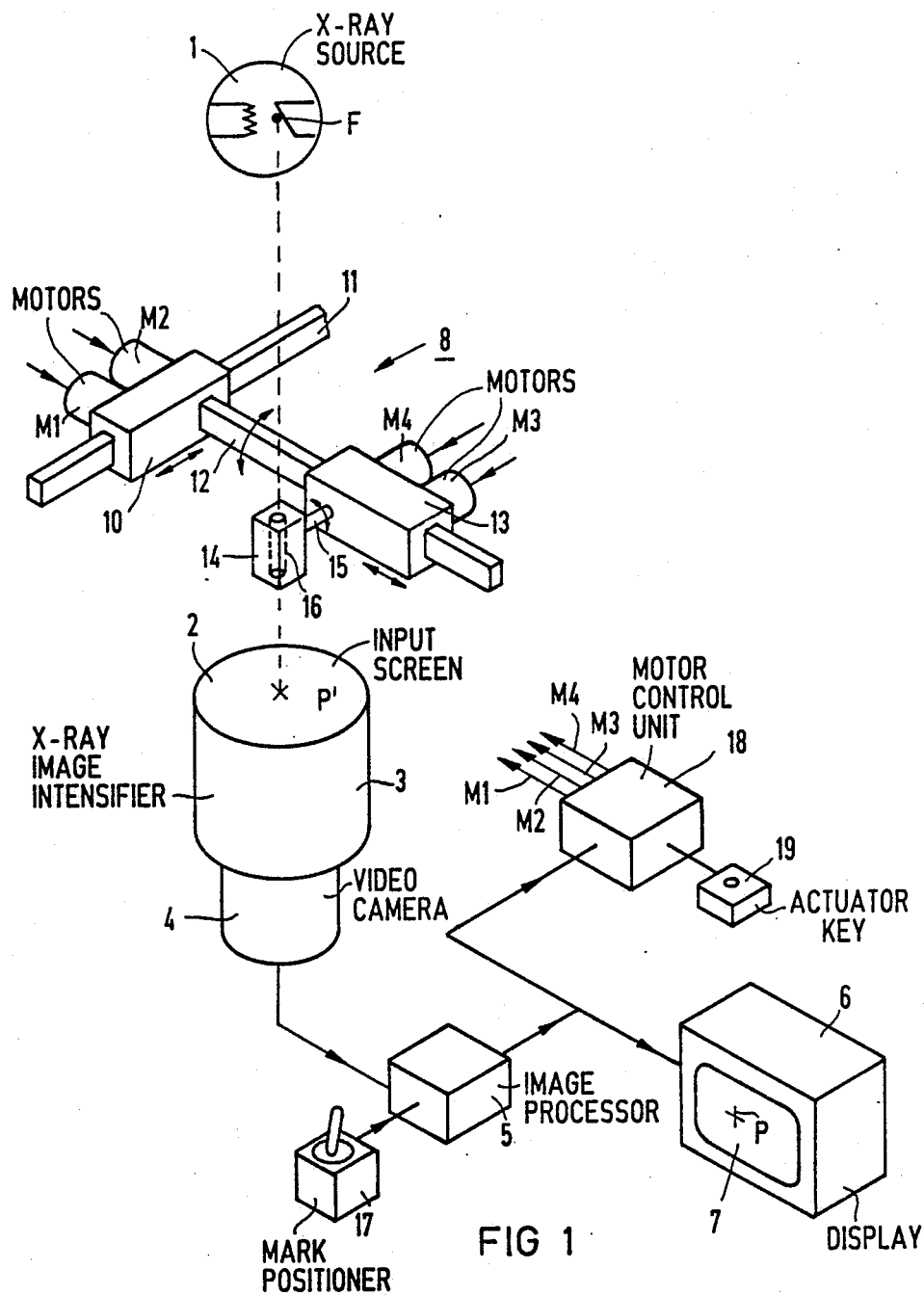
FIG. 1 is a schematic perspective view of an x-ray examination apparatus with a biopsy assembly constructed in accordance with the principles of the present invention.

The x-ray examination apparatus shown in FIG. 1 includes an x-ray tube 1 having a focus F from which a ray pyramid emanates. After it has penetrated an examination subject (not shown in FIG. 1), the ray pyramid is incident on the input luminescent screen 2 of an x-ray image intensifier 3 that is followed by a video camera 4 that records the image of the output luminescent screen of the x-ray image intensifier 3. The output signals of the video camera 4 proceed via an image processor 5 to a video monitor 6 having a picture screen 7 on which the x-ray picture of the examination subject is portrayed.

A biopsy assembly generally referenced 8 is arranged at a fixed distance from the input luminescent screen 2 between the x-radiator 1 and the examination subject. The biopsy assembly has a first carriage 10 that is displaceable on a rectangular guide rod 11 by a motor M1. A further rectangular guide rod 12 is attached to the first carriage 10, the guide rod 12 being pivotable around its longitudinal axis with a motor M2 such that a second carriage 13, displaceable on the guide rod 12 with a motor M3, follows the pivot motion of the guide rod 12. A guide element 14 for the biopsy needle is attached to the second carriage 13 so as to be pivotable around an axis 15 with a motor M4. The guide element 14 has a channel 16 through which a puncture of the examination subject situated below the guide element 14 can be made with the biopsy needle (not shown).

A joy stick 17 is provided for the determination of the paracentesis point for the biopsy needle, the joy stick 17 being connected to the image processor 5 so that, dependent on the position of the joy stick 17, a mark P is mixed into the x-ray picture portrayed on the picture screen 7. The mark P is arbitrarily movable on the picture screen with the joy stick 17 and thus is positionable to a diagnostically relevant region visible in the x-ray picture.

The image processor 5 forwards signals corresponding to the position of the mark P to a motor control unit 18. As soon as a key 19 connected thereto is pressed, the motor control unit 18 actuates the motors M1 through M4 such that the guide element 14 is moved into a position relative to the examination subject such that the longitudinal axis of its channel 16 process through the paracentesis point pertaining to the diagnostically relevant region. The paracentesis point—due to the fact that the x-ray picture arises on the basis of central projection—lies on a straight line proceeding through the diagnostically relevant region and the focus F of the x-radiator 1. The motor control unit 18 automatically actuates the motors M1 through M4 such that the longitudinal axis (shown with broken lines in FIG. 1) of the channel 16 of the guide element 14 proceeds through the focus F of the x-ray tube 1 and through the fictitious position P′ of the mark on the input luminescent screen 2 of the x-ray image intensifier 3. It is thus assured that the puncture channel of the biopsy needle that is introduced in to the examination subject through the channel 16 of the guide element 14 leads to the diagnostically relevant region inside the examination subject.

Figure 2:
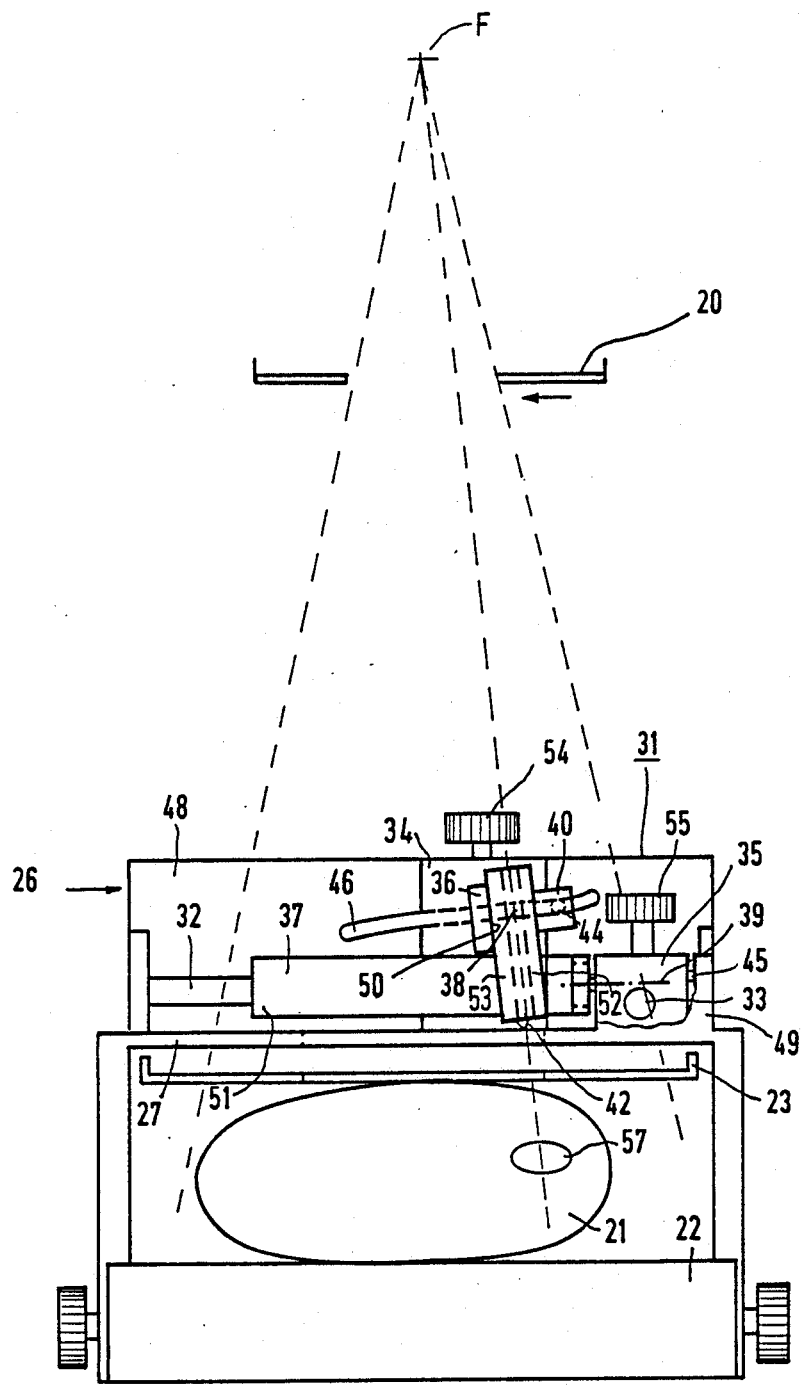
FIG. 2 is a partly schematic side view of an x-ray examination apparatus including the biopsy assembly of the invention.
Figure 3:
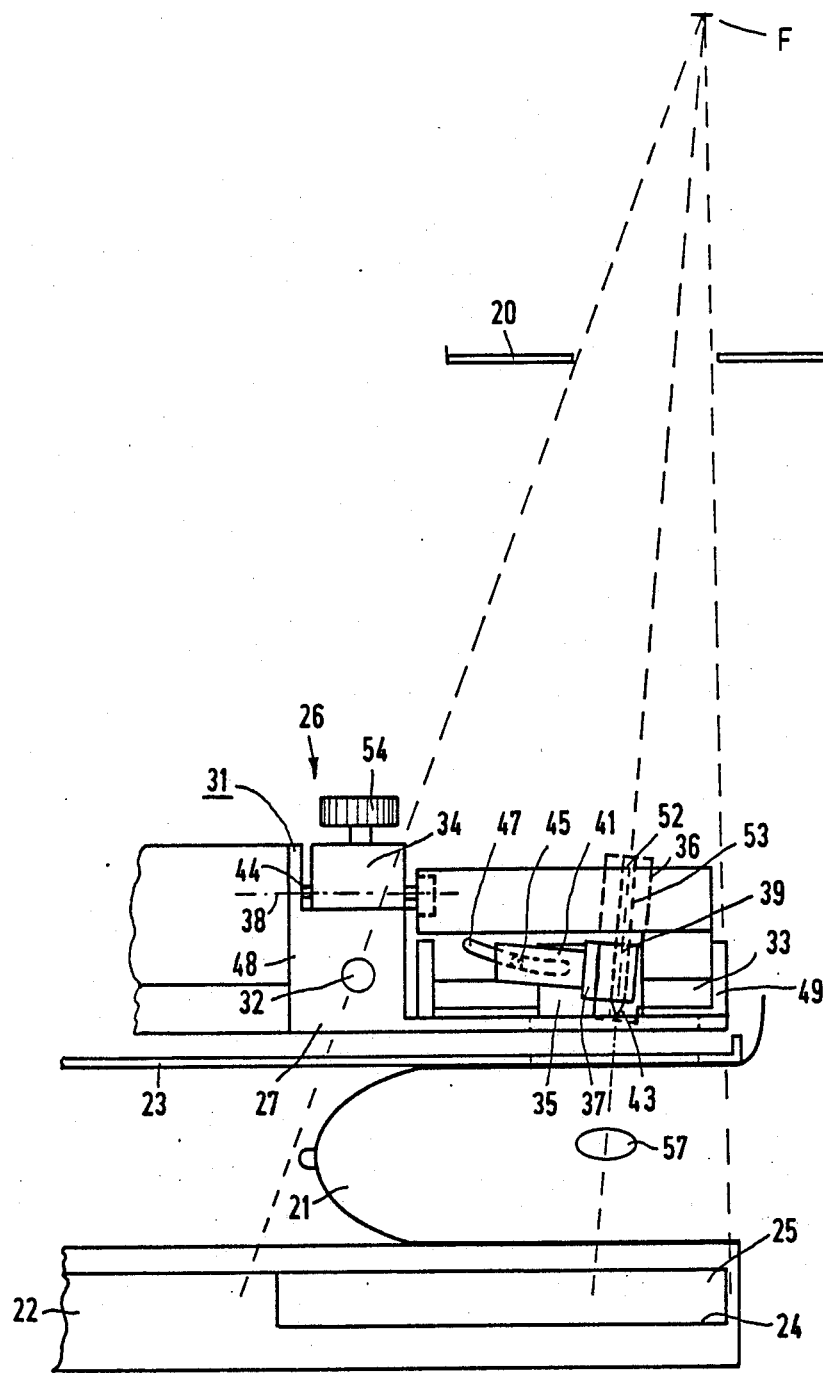
FIG. 3 is a further side view of the x-ray examination apparatus of FIG. 2.
Figure 4:
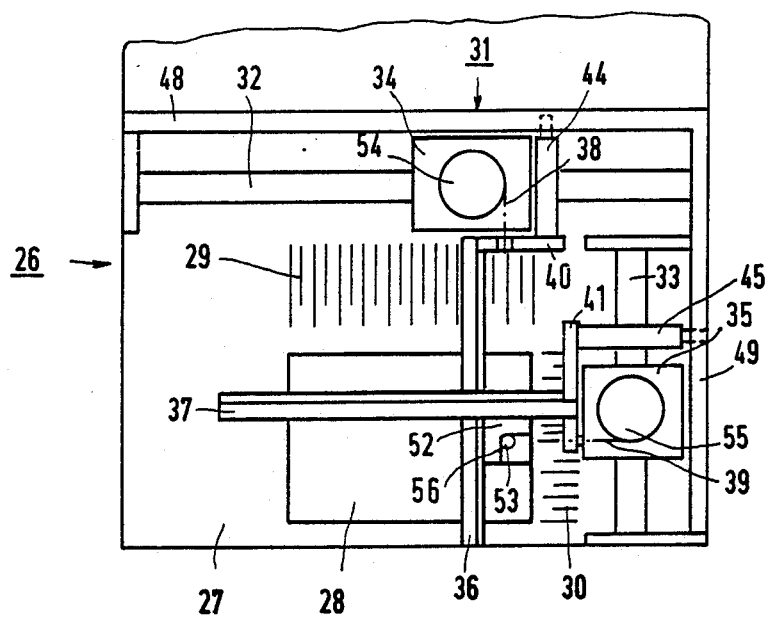
FIG. 4 is a plan view of the biopsy assembly of the x-ray examination apparatus according to FIG. 2 and FIG. 3.

FIGS. 2 through 4 show an x-ray examination apparatus having another embodiment of the biopsy assembly of the invention. In detail, this x-ray examination apparatus includes an x-radiator of which only the focus F is shown. The x-ray beam emanating therefrom is gated with a primary radiation diaphragm 20 such that a ray pyramid (indicated with broken lines) having a rectangular cross section arises, the examination subject 21, for example a female breast, being situated in the beam path thereof. The examination subject 21 lies on a bearing plate 22 and can be compressed by a compression plate 23 of radiation-transmissive material that has an opening and is height-adjustable relative to the bearing plate 22. The bearing plate 22 has a receptacle 24 into which an x-ray film cassette 25 can be introduced.

The biopsy assembly generally referenced 26 is attached above the compression plate 23 at a fixed distance from the focus F of the x-radiator. The biopsy assembly 26 has a base plate 27 of radiation-transmissive material parallel to the bearing plate 22, the base plate 27 being provided with a rectangular recess 28 adapted to the opening of the compression plate 23 and through which the examination subject 21 is accessible.

Scales 29 and 30 are respectively provided parallel to two edges of the recess 28 neighboring one another. The division marks of the scales 29 and 30 are composed of a radiation-impermeable material, for example lead, and since they are situated in the ray pyramid emanating from the focus F, can be imaged on an x-ray exposure together with the examination subject 21.

The base plate 27 has an edge 31 to which two guide rods 32 and 33 respectively proceeding parallel to the scales 29 and 30 and to the base plate 27 are attached. The guide rods 32 and 33 are arranged in different planes. Guide blocks 34 and 35 are respectively longitudinally displaceable on the rods 32 and 33. Each guide block 34 and 35 carries a respective ruler 36 and 37 having a rectangular cross-section whose longitudinal axis proceeds at a right angle to the corresponding guide rod 32 or 33, and parallel to the base plate 27. The rulers 36 and 37 (also arranged in different planes) have a length such that they extend through the entire radiation pyramid in every position. Each ruler has a respective angled section 40 and 41 at its respective end adjacent to the corresponding guide rod 32 or 33. Each ruler has a mark 42 or 43 attached to the respective angled section 40 or 41 at a distance from the longitudinal axis of the ruler 36 or 37 which interacts with the respective scale 29 or 30. The rulers are attached to the respective guide blocks 34 and 35 pivotable around respective axes 38 and 39 proceeding parallel to the longitudinal axes of the rulers. Pivoting of the rulers 36 and 37 when the rulers are displaced along the respective guide rods 32 and 33 ensues entrained such that the focus X of the x-radiator, the mark 42 or 43, and the axis 38 or 39 lie in a common plane. To this end, respective projections 44 and 45 are provided at the angled section 40 and 41 of the rulers 36 and 37. The projections 44 and 45 respectively engage grooves 46 and 47 which are stationary relative to the rulers 36 and 37. The grooves 46 and 47 are respectively disposed in a section 48 or 49 of the edge 31 of the base plate 27 proceeding parallel to the respective guide rod 32 or 33. The dimension by which the grooves 46 and 47 in the described exemplary embodiment deviate from a straight-line course parallel to the guide rods 32 or 33 corresponds to the cosine of the angle described between the respective common plane and the corresponding guide rod 32 or 33 multiplied by the distance between the respective axis 38 or 39 and the associated projection 44 and 45.

The rulers 36 and 37 each have a seating surface 50 or 51 for a cubic guide element 52 for a biopsy needle which is magnetically held in the angle formed by the seating surfaces 50 and 51 of the rulers 36 and 37. The seating surfaces 50 and 51 of the rulers 36 and 37 each proceed parallel to the common plane in which the focus F of the x-radiator, the mark 42 or 43, and the respective axis 38 or 39 are situated. A channel 53 for the biopsy needle (not shown) is provided in the guide element 52 essentially corresponding in diameter to the biopsy needle employed. The channel 53 is arranged in the guide element 52 such that it proceeds parallel to the bearing surfaces 50 and 51, at a respective distance therefrom corresponding to the distance between the seating surfaces 50 or 51 and the associated aforementioned common planes.

It is thus assured that the course of the longitudinal axis of the channel 53 corresponds to the intersecting straight line of two planes in every position of the rulers 36 and 37, these planes each proceeding parallel to one of the scales 29 or 30 and through the mark 43 or 42 interacting with the other scale 30 or 29, as well as through the focus F of the x-radiator. This means that the longitudinal axis of the channel 53 proceeds through the focus F of the x-radiator in every position of the rulers 36 and 37. When a diagnostically relevant region visible on the x-ray exposure and situated inside the examination subject 21 is to be punctured, it suffices to identify the coordinates of the region with reference to the scales 29 and 30 imaged on the x-ray exposure and to bring the rulers 36 and 37 into a position by adjusting the guide blocks 34 and 35 such that marks 42 and 43 are directed onto the division marks of the scales 29 and 30 corresponding to the coordinates of the diagnostically relevant region. A paracentesis point for the biopsy needle is thus obtained that, due to the fact that the x-ray picture arises by central projection, lies on a straight line that proceeds through the focus F of the x-radiator and through the diagnostically relevant region. Since, moreover, the longitudinal axis of the channel 53 of the guide element 52 proceeds through the focus F of the x-radiator when the guide element 52 is inserted into the angle formed by the bearing surfaces 50 and 51 of the rulers 36 and 37, it is automatically guaranteed that the puncture channel of the biopsy needle introduced into the examination subject 21 through the channel 53 of the guide element 52 leads to the diagnostically relevant region. It is expedient to lock the guide blocks 34 and 35 before the puncturing by actuating clamp screws 54 and 55 acting on the guide rods 32 and 33.

For producing standard x-ray exposures, the rulers 36 and 37 are respectively moved into a standby position in which they are situated outside of the ray pyramid.

As indicated in FIGS. 2 through 4, the guide element 52 is composed of two parts whose joint contains the channel 53.

The means for positioning the guide device set forth in conjunction with the exemplary embodiments are to be understood as being only by way of example. These can also be differently fashioned within the framework of the invention insofar as it is assured that they always keep the channel of the guide device aligned to the focus of the x-radiator. The guide device can also be fashioned in a way different from that set forth in conjunction with the exemplary embodiments.

I claim as my invention:

1. In an x-ray diagnostics installation having an x-ray source with a focus from which an x-ray beam emanates, and an x-radiation receiver disposed for receiving x-radiation attenuated by a diagnostically relevant region in a patient between said x-ray source and said x-radiation receiver, the improvement of a guiding and positioning assembly for a biopsy needle comprising:
   means for determining a paracentesis point on said patient for said biopsy needle lying on a straight line between said focus and said diagnostically relevant region;
   a guide element for said biopsy needle having a channel therein for holding said biopsy needle in said channel, said channel having a longitudinal axis; and
   means for automatically positioning said guide element so that said longitudinal axis of said channel always proceeds through said focus.

2. The improvement of claim 1 wherein said x-radiation receiver includes means for generating electrical signals corresponding to the x-radiation incident thereon, and wherein said x-ray diagnostics installation further includes a video monitor for displaying on image of said diagnostically relevant region in said patient based on said electrical signals, said improvement further comprising:
   means for generating a mark and for mixing said mark into said image on said video monitor;
   means for moving said mark in said x-ray image on said video monitor; and
   means for controlling said means for automatically positioning said guide element so that said longitudinal axis of said channel always proceeds through a fictitious position of said mark in said image on said video monitor.

3. The improvement of claim 1 wherein said x-radiation receiver includes means for taking an exposure of said diagnostically relevant region in said patient, and wherein said means for determining a paracentesis point comprises:
   first and second scales disposed in said x-ray beam and defining an angle and being imagable on said x-radiation receiver; and
   first and second marks co-movable with said means for automatically positioning said guide element, said first mark interacting with said first scale and said second mark interacting with second scale, each of said marks being disposed relative to said channel so that the longitudinal axis of said channel proceeds in a plane intersecting with said first scale at a point thereon aligned with said first mark and parallel to said second scale and in a plane intersecting said second scale at a point thereon aligned with second mark and proceeding parallel to said first scale.

4. The improvement of claim 3 wherein said x-ray beam is a ray pyramid having edges, and wherein said scales are respectively disposed at said edges of said ray pyramid, and wherein said means for automatically positioning said guide element comprises:
   first and second rulers disposed in different planes, said first and second rulers being respectively associated with said first and second scales;
   means for displacing said first ruler along a right angle relative to said first scale;
   means for displacing said second ruler along a right angle relative to said second scale;
   each of said first and second rulers having a length such that each ruler extends through the entire ray pyramid at each position of said rulers;
   each of said rulers having a longitudinal axis and said first mark being attached to said first ruler at a distance from the longitudinal axis of said first ruler and said second mark being attached to said second ruler at a distance from the longitudinal axis of said ruler;
   means for pivoting said first ruler around a first pivot axis proceeding parallel to said longitudinal axis of said first ruler during displacement of said first ruler along said first scale so that said focus, said first mark, said first pivot axis and said longitudinal axis of said channel always lie in a common plane;

means for pivoting said second ruler around a second pivot axis proceeding parallel to the longitudinal axis of said second ruler during displacement of said second ruler along said second scale so that said focus, said second mark, said second pivot axis and said longitudinal axis of said channel always lie in a further common plane;

a surface on said first ruler proceeding parallel to said common plane and extending along the entire length of said first ruler;

a surface on said second ruler proceeding parallel to said further common plane and extending over the entire length of said second ruler, said surfaces of said first and second rulers defining an angle therebetween;

said guide element having a cuboid shape and being received in said angle formed by said surfaces of said first and second rulers; and means for moving each of said first and second rulers to a standby position outside of said ray pyramid.

5. The improvement of claim 4 wherein said means for pivoting said first ruler comprises a first projection on said first ruler and a stationary receptacle engaged by said first projection, said first projection being spaced from and parallel to said first pivot axis, and wherein said means for pivoting said second ruler comprises a second projection on said second ruler and a stationary receptacle engaged by said second projection, said second projection being spaced from and parallel to said second pivot axis.

6. The improvement of claim 4 further comprising:
means for locking said first ruler in a selected position; and
means for locking said second ruler in a selected position.

7. The improvement of claim 3 wherein said first and second marks are respectively disposed at such locations relative to said first and second scales that parallax errors are avoided.

8. The improvement of claim 1 further comprising means for releasably retaining said guide element in said means for automatically positioning said guide element.

9. The improvement of claim 8 wherein said means for releasably retaining is a means for magnetically holding said guide element in said means for automatically positioning said guide element.

10. The improvement of claim 1 wherein said guide element consists of two mating sections, said sections being joined at said channel.

* * * * *